United States Patent
Amino et al.

(10) Patent No.: US 7,329,427 B2
(45) Date of Patent: Feb. 12, 2008

(54) PROCESS FOR PRODUCING γ-HYDROXYAMINO ACID DERIVATIVES AND MONATINS

(75) Inventors: Yusuke Amino, Kawasaki (JP); Shigeru Kawahara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 753 days.

(21) Appl. No.: 10/397,407

(22) Filed: Mar. 27, 2003

(65) Prior Publication Data

US 2003/0228403 A1    Dec. 11, 2003

(30) Foreign Application Priority Data

Apr. 1, 2002    (JP)    ............................... 2002-098515

(51) Int. Cl.
*A23L 1/236*    (2006.01)
(52) U.S. Cl. .......................................... 426/548; 564/1
(58) Field of Classification Search ................ 426/548; 564/1
See application file for complete search history.

(56) References Cited

U.S. PATENT DOCUMENTS 5,128,482 A    7/1992    Olivier et al.
5,994,559 A    11/1999    Abushanab et al.
2003/0228403 A1    12/2003    Amino et al.

FOREIGN PATENT DOCUMENTS

JP    2002-60382    *    2/2002

OTHER PUBLICATIONS

V. Helaine, et al., Tetrahedron: Asymmetry, vol. 9, No. 21, pp. 3855-3861, XP-004143701, "Chemo-Enzymatic Synthesis of the Four Stereoisomers of 4-Hydroxy-4-Methylglutamic Acid", Nov. 6, 1998.
U.S. Appl. No. 10/397,407, filed Mar. 27, 2003, Amino, et al.
U.S. Appl. No. 10/109,719, filed Apr. 1, 2002, Amino, et al.
U.S. Appl. No. 10/860,018, filed Jun. 4, 2004, Amino, et al.
U.S. Appl. No. 10/856,756, filed Jun. 1, 2004, Amino, et al.
U.S. Appl. No. 10/992,795, filed Nov. 22, 2004, Amino, et al.

* cited by examiner

*Primary Examiner*—Leslie Wong
(74) *Attorney, Agent, or Firm*—Oblon, Spivak, McClelland, Maier & Neustadt, P.C.

(57) ABSTRACT

Dihydroisoxazole derivatives are conveniently converted to γ-hydroxyamino acid derivatives which are important as various synthetic intermediates by a catalytic hydrogenation reaction. High-purity monatins which may be used as sweeteners or ingredients thereof can be obtained by subjecting a 5-indolylmethyl-4,5-dihydroisoxazole-3,5-dicarboxylic acid to catalytic hydrogenation.

20 Claims, No Drawings

PROCESS FOR PRODUCING γ-HYDROXYAMINO ACID DERIVATIVES AND MONATINS

CROSS REFERENCE TO RELATED APPLICATIONS

This application claims priority to Japanese Patent Application No. 2002-098515, which was filed on Apr. 1, 2002, and which is incorporated herein by reference in its entirety.

BACKGROUND OF THE INVENTION

1. Field of the Invention

The present invention relates to novel processes for producing γ-hydroxyamino acid derivatives, especially monatins. More specifically, it relates to process in which dihydroisoxazole derivatives are converted to γ-hydroxyamino acid derivatives which are important as synthetic intermediates. The present invention more especially relates to processes in which dihydroisoxazole derivatives having an indolyl group are converted to monatins (including stereoisomers, salts thereof, and those with one or more protected functional groups), which are excellent as sweeteners or active ingredients thereof.

2. Discussion of the Background

In recent years, with the higher level of eating habits, obesity due to the excessive intake of sugar in particular and the consequent diseases have become a serious health issue. Accordingly, the development of low-caloric (low-calorie) sweeteners that replace sugar has been in high demand. For these sweeteners, characteristics such as low calorie content, safety, stability to heat or acid, sweetness quality, and costs have to be taken into consideration in addition to the degree of sweetness (sweetening potency).

Various sweeteners have been currently in use or proposed. For example, aspartame is a sweetener with a high degree of sweetness which is capable of industrial mass-production and has actually found wide acceptance. Aspartame is excellent in regard to safety and sweetness quality. Further, aspartame derivatives have been increasingly studied. In addition to aspartame and aspartame derivatives, other sweetening materials having various characteristics as sweeteners have been proposed and studied for actual use. For example, thaumatin, glycyrrhizin, and stevioside derived from plants, which are present in nature and can be collected in large quantities, have been currently used as natural sweeteners.

Monatin is a natural amino acid derivative isolated from the bark of the roots of *Schlerochiton ilicifolius*, a plant that grows wild in the north-western Transvaal region of South Africa. Monatin has been reported to have a structure which corresponds to (2S,4S)-2-amino-4-carboxy-4-hydroxy-5-(3-indolyl)pentanoic acid, or alternatively, (2S,4S)-4-hydroxy-4-(3-indolylmethyl)-glutamic acid; see the structural formula (3) (R. Vleggaar et al., *J. Chem. Soc. Perkin Trans.*, pp. 3095-3098 (1992)).

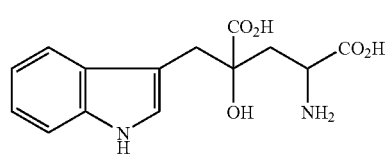

(3)

The degree of sweetness of the (2S,4S) compound derived from the natural plant has been determined to be 800 times or 1,400 times that of sucrose (see, R. Vleggaar et al., *J. Chem. Soc. Perkin Trans.*, pp. 3095-3098 (1992)).

Various processes for producing monatin have been reported (see, P. J. van Wyk et al., ZA 87/4288; C. W. Holzapfel et al., *Synthetic Communications*, vol. 24(22), pp. 3197-3211 (1994); E. Abushanab et al., U.S. Pat. No. 5,994,559 (1999); and K. Nakamura et al., *Organic Letters*, vol. 2, pp. 2967-2970 (2000)). However, there is no appropriate industrial process for producing monatin.

In *Synthetic Communications*, vol. 24(22), pp. 3197-3211 (1994) and U.S. Pat. No. 5,128,482, dihydroisoxazole derivatives represented by the following structural formula (4) are reduced with sodium amalgam (NaHg) to convert the same to monatins represented by the following structural formula (3).

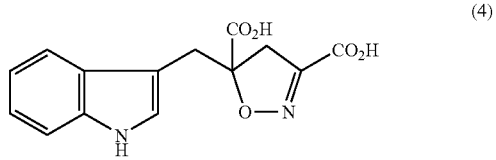

(4)

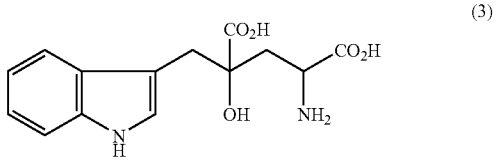

(3)

However, since this process uses a mercury compound having a high toxicity, it is extremely dangerous in operation. When the products are used as sweeteners, a procedure for thoroughly removing mercury with an ion exchange resin or the like after completion of the reaction is indispensable. Although U.S. Pat. No. 5,128,482 broadly claims "chemically reducing" a compound of the structural formula (4) to obtain a compound of the structural formula (3), only the use of sodium amalgam is demonstrated in the Examples. Moreover, reagents, reaction conditions and the like are neither specifically claimed nor described in detail. In the description of the chemical reduction step, only sodium amalgam (amalgam reduction), cyanoborohydride (hydride reduction) and sodium (molten metal reduction) are listed as reducing agents. There is no description of catalytic hydrogenation. Moreover, it is known that reduction of an aromatic ring such as an indolyl group proceeds as a side reaction to catalytic hydrogenation. In other words, the hydrogenation reaction for the conversion as described above has not been reported.

The conversion of a diethyl 5-methyl-4,5-dihydroisoxazole-3,5-dicarboxylate (the compound of the general formula (1) in which $R^1$ is a methyl group and $R^2$ and $R^3$ are each an ethyl group) to a γ-hydroxyamino acid derivative has been reported (see, V. Helaine et al., *Tetrahedron: Asymmetry*, vol. 9, pp. 3855-3861 (1998)).

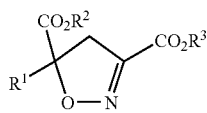
(1)

When the compound is reacted as such, conversion to a lactam occurs and the reaction is therefore conducted in the presence of benzoic anhydride to obtain an N-benzoyl derivative. Thus, although a γ-hydroxyamino acid derivative is obtained by the catalytic hydrogenation reaction of the derivative in which $R^1$ is a methyl group, the reaction solution is heated to reflux overnight in 6 N-hydrochloric acid aqueous solution for removal of the benzoyl group. However, when a functional group extremely labile to an acid, such as an indolylmethyl group is present in a molecule, such severe deprotection conditions cannot be applied. Accordingly, a conversion method that does not require such a procedure is desired.

Thus, there remains a need for a practical and simple process for converting dihydroisoxazole derivatives represented by the structural formula (1) to the γ-hydroxyamino acid derivatives of formula (2).

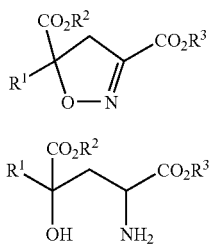
(1)

(2)

There also remains a need for a practical and simple process for converting dihydroisoxazole derivatives represented by the structural formula (4) and the like to the monatins represented by the structural formula (3).

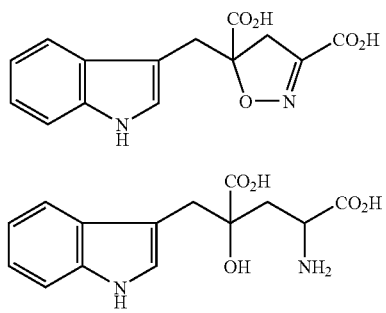
(4)

(3)

SUMMARY OF THE INVENTION

Accordingly, it is one object of the present invention to provide novel methods for preparing γ-hydroxyamino acid derivatives of formula (2) and salts thereof.

It is another object of the present invention to provide novel methods for converting a dihydroisoxazole derivative represented by the structural formula (1) or a salt thereof to a γ-hydroxyamino acid derivative of formula (2) or a salt thereof.

It is another object of the present invention to provide novel methods for converting a dihydroisoxazole derivative represented by the structural formula (1) or a salt thereof to a γ-hydroxyamino acid derivative of formula (2) or a salt thereof, which does not employ toxic reagents, such as sodium amalgam.

It is another object of the present invention to provide novel methods for converting a dihydroisoxazole derivative represented by the structural formula (1) or a salt thereof to a γ-hydroxyamino acid derivative of formula (2) or a salt thereof, which does not employ harsh reaction conditions, such as heating to reflux in a strong acid.

It is another object of the present invention to provide novel methods for preparing monatin of formula (3) and salts thereof.

It is another object of the present invention to provide novel methods for converting a dihydroisoxazole derivative represented by the structural formula (4) or a salt thereof to monatin of formula (3) or a salt thereof.

It is another object of the present invention to provide novel methods for converting a dihydroisoxazole derivative represented by the structural formula (4) or a salt thereof to monatin of formula (3) or a salt thereof, which does not employ toxic reagents, such as sodium amalgam.

It is another object of the present invention to provide novel methods for converting a dihydroisoxazole derivative represented by the structural formula (4) or a salt thereof to monatin formula (3) or a salt thereof, which does not employ harsh reaction conditions, such as heating to reflux in a strong acid.

Thus, the problem to be solved by the present invention is to develop a convenient process for: (1) converting dihydroisoxazole derivatives to γ-hydroxyamino acid derivatives, which are important as various synthetic intermediates; and further (2) converting specific dihydroisoxazole derivatives to monatins that can be expected to be put to practical use as sweeteners.

The present inventors have assiduously conducted investigations to solve the problem. That is, they have studied various catalytic hydrogenation reactions on the compounds represented by the general formula (1) and the structural formula (4) described above, especially catalysts, solvents, additives, hydrogen pressure and the like. Consequently, they have found an appropriate process in which the compounds represented by the general formula (2) or the structural formula (3) described above can be obtained in high yield.

Thus, the above-noted and other objects, which will become apparent during the following detailed description, have been achieved by the inventors' discovery that a dihydroisoxazole derivative represented by the structural formula (1) or a salt thereof may be conveniently converted to a γ-hydroxyamino acid derivative of formula (2) or a salt thereof by catalytically reducing the dihydroisoxazole derivative represented by the structural formula (1).

The inventors have further discovered that when a heterogeneous catalyst is used as a catalyst and ammonia or the like is used as a base, an ammonium salt of the desired product is obtained by simply removing the catalyst from the reaction solution after the reaction by filtration and concentrating the reaction solution thus obtained.

In addition, it has been found that when this process is applied to the production of monatins, high-purity desired products are obtained as crystals by a safe and simple procedure.

Thus, the present invention provides a novel process for conversion of dihydroisoxazole derivatives to γ-hydroxyamino acid derivatives and a process for producing monatins expected to be useful as sweeteners. These findings have led to the completion of the present invention. According to the present process, monatins can easily be obtained without using toxic sodium amalgam as performed by C. W. Holzapfel et al. and without employing the severe deprotection method by heating to reflux with a strong acid as performed by V. Helaine et al.

That is, the present invention provides a process for the conversion of dihydroisoxazole derivatives to γ-hydroxyamino acid derivatives through a catalytic hydrogenation reaction, and especially to an efficient process for the production of monatins.

DETAILED DESCRIPTION OF THE PREFERRED EMBODIMENTS

The embodiments for the present invention are described in detail below.

In a first embodiment, the present invention provides a process for producing a γ-hydroxyamino acid derivative represented by the following general formula (2) or a salt thereof, which comprises subjecting a dihydroisoxazole derivative represented by the following general formula (1) or a salt thereof to catalytic hydrogenation

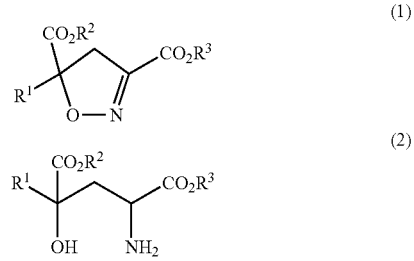

$R^1$ represents a hydrogen atom, or a carboxyalkyl, an alkyl, an aryl, an aralkyl, or one or more heterocyclic ring(s)-containing hydrocarbon group (radical) each having up to 20 carbon atoms;

$R^2$ and $R^3$ each, independently of the other, represents a hydrogen atom, an alkyl group having up to 5 carbon atoms, or an aralkyl group having up to 12 carbon atoms; and each asymmetric carbon atom may have a steric configuration of (R), (S), or (RS).

In the context of the present invention, the term "(RS)" as used to describe the configuration of a single asymmetric carbon atom means that the compound is a mixture of essentially equal amounts of the compounds which have the (R) and (S) configurations at that carbon atom.

When the form of a salt(s) is possible, for example when $R^2$ and/or $R^3$ is a hydrogen atom, the dihydroisoxazole derivative and/or the γ-hydroxyamino acid derivative may take the form of a salt(s).

As noted above, $R^1$ may be a carboxyalkyl group having up to 20 carbon atoms. Specific examples of the carboxyalkyl group for $R^1$ include carboxymethyl, carboxyethyl, carboxylpropyl, carboxybutyl, carboxypentyl, carboxyhexyl, carboxyheptyl, carboxyloctyl, carboxyldecyl, and carboxydodecyl.

$R^1$ may also be an alkyl group having up to 20 carbon atoms. Specific examples of the alkyl group for $R^1$ include methyl, ethyl, n-propyl, iso-propyl, n-butyl, iso-butyl, sec-butyl, t-butyl, n-pentyl, iso-pentyl, sec-pentyl, neo-pentyl, n-hexyl, iso-hexyl, sec-hexyl, n-heptyl, iso-heptyl, sec-heptyl, n-octyl, iso-octyl, sec-octyl, n-nonyl, iso-nonyl, sec-nonyl, n-decyl, iso-decyl, sec-decyl, n-dodecyl, iso-decyl, sec-dodecyl, tetradecyl, hexadecyl, octadecyl, and dodecyl.

$R^1$ may further be an aryl group having up to 20 carbon atoms. Specific examples of the aryl group for $R^1$ include phenyl, lower-alkyl-substituted phenyl (including tolyl, xylyl, and mesityl), amino-substituted phenyl, hydroxyl-substituted phenyl, lower-alkoxy-substituted phenyl, halo-substituted phenyl, cyano-substituted phenyl, nitro-substituted phenyl, naphthyl, lower-alkyl-substituted naphthyl, amino-substituted naphthyl, hydroxyl-substituted naphthyl, lower-alkoxy-substituted naphthyl, halo-substituted naphthyl, cyano-substituted naphthyl, nitro-substituted naphthyl, biphenyl, lower-alkyl-substituted biphenyl, amino-substituted biphenyl, hydroxyl-substituted biphenyl, lower-alkoxy-substituted biphenyl, halo-substituted biphenyl, cyano-substituted biphenyl, and nitro-substituted biphenyl.

$R^1$ may also be an aralkyl group having up to 20 carbon atoms. Specific examples of the aralkyl group for $R^1$ include benzyl, lower-alkyl-substituted benzyl, amino-substituted benzyl, hydroxyl-substituted benzyl, lower-alkoxy-substituted benzyl, halo-substituted benzyl, cyano-substituted benzyl, nitro-substituted benzyl, phenylethyl, lower-alkyl-substituted phenylethyl, amino-substituted phenylethyl, hydroxyl-substituted phenylethyl, lower-alkoxy-substituted phenylethyl, halo-substituted phenylethyl, cyano-substituted phenylethyl, and nitro-substituted phenylethyl.

$R^1$ may also be a hydrocarbon group which is substituted with one or more heterocyclic rings and which contains up to 20 total carbon atoms. Specific examples of the heterocyclic ring(s)-containing hydrocarbon group having up to 20 carbon atoms for $R^1$ include branched and unbranched, saturated and unsaturated hydrocarbon groups which are substituted with a heterocyclic ring selected from the group consisting of indolyl, pyrolyl, morpholinyl, pyridinyl, pyrimidinyl, piperazinyl, furanyl, pyranyl, and thiophenyl, provided that the total number of carbon atoms in the group is no more than twenty. In this case, $R^1$ may be, e.g., an indolyl-lower-alkyl group, a pyrolyl-lower-alkyl group, a morpholinyl-lower-alkyl group, a pyridinyl-lower-alkyl group, a pyrimidinyl-lower-alkyl group, a piperazinyl-lower-alkyl group, a furanyl-lower-alkyl group, a pyranyl-lower-alkyl group, or a thiophenyl-lower-alkyl group.

In the above described formulas, $R^1$ is preferably a benzyl group or a 3-indolylmethyl group. Preferably, a benzene ring or an indole ring in the substituent group may be substituted with at least one of a halogen atom (such as an iodine atom, a bromine atom, a chlorine atom, a fluorine atom or the like), a hydroxyl group, an alkyl group having up to 3 carbon atoms, an alkoxy group having up to 3 carbon atoms, and an amino group.

Especially when $R^1$ is a 3-indolylmethyl group, it is advantageous for the production of monatins.

In the case of $R^2$ and $R^3$, specific examples of the alkyl group include methyl, ethyl, n-propyl, iso-propyl, n-butyl, iso-butyl, sec-butyl, t-butyl, n-pentyl, iso-pentyl, sec-pentyl, and neo-pentyl, while specific examples of the aralkyl group include benzyl, lower-alkyl-substituted benzyl, amino-substituted benzyl, hydroxyl-substituted benzyl, lower-alkoxy-substituted benzyl, halo-substituted benzyl, cyano-substituted benzyl, nitro-substituted benzyl, phenylethyl, lower-alkyl-substituted phenylethyl, amino-substituted phenylethyl, hydroxyl-substituted phenylethyl, lower-alkoxy-substituted phenylethyl, halo-substituted phenylethyl, cyano-substituted phenylethyl, and nitro-substituted phenylethyl.

In the compounds of formulae (1) and (4), there is an asymmetric carbon atom in the dihydroisoxazole ring, and this asymmetric carbon atom may exist in either the (R) or (S) configuration. Moreover, the compounds of formulae (1) and (4) which are used as the starting materials in the present methods may exist as either a racemic mixture (in which the (R)-optical isomer and (S)-optical isomer are present in approximately equal amounts) or as an optically active compound (in which either the (R)-optical isomer or (S)-optical isomer is present in a significant excess).

Similarly, in the compounds of formulae (2) and (3), there are two asymmetric carbon atoms (excluding any additional asymmetric carbon atoms in $R^1$ in the compounds of formula (2), which may independently of each other exist in either the (R) or (S) configuration. Thus, the compounds of formulae (2) and (3) may exist as four different optical isomers: (R,R), (S,S), (R,S), and (S,R). The (R,R) and (S,S) configurations represent one pair of optical isomers, while the (R,S) and (S,R) configurations represent another pair of optical isomers; the remaining relationships are of a diastereomeric nature. Thus, the compounds of formulae (2) and (3) may exist as: (1) a mixture of all four optical isomers; (2) a substantially pure racemic mixture of one pair of optical isomers (i.e., a mixture in which the (R,R)-optical isomer and (S,S)-optical isomer are present in approximately equal amounts or in which the (R,S)-optical isomer and (S,R)-optical isomer are present in approximately equal amounts); (3) an optically active compound (a pure optical isomer or a mixture which is enriched in either the (R,R)-optical isomer, (S,S)-optical isomer, (R,S)-optical isomer, or (S,R)-optical isomer); or any intermediate mixture.

In the catalytic hydrogenation reaction, the catalyst may be selected from rhodium catalysts such as a rhodium-active carbon catalyst and a rhodium-alumina catalyst; palladium catalysts such as a palladium-active carbon catalyst and a palladium chloride catalyst; ruthenium catalysts such as a ruthenium-active carbon catalyst; nickel catalysts such as Raney nickel; and platinum catalysts such as a platinum-active carbon catalyst.

It is advisable to use a solvent in the catalytic hydrogenation reaction, and the type of the solvent is not particularly limited so long as it is inert to the reaction. Water, an alcohol (methanol, ethanol, propanol, etc.), or a mixed solvent of water and one or more alcohols can preferably be used. In the case of an alcohol, a mixture of more than one alcohol can naturally be used.

The catalytic hydrogenation reaction can be conducted in the presence or absence of a base. When a base is a used, organic and/or inorganic base(s) such as ammonia, amines, sodium hydroxide, potassium hydroxide, sodium carbonate, and sodium bicarbonate can be used.

When water is used as a solvent, the pH value of the solution is preferably in the alkaline range. The pH value is more preferably on the order of from 8 to 14.

The hydrogenation reaction is preferably conducted under a hydrogen atmosphere. At this time, the hydrogen pressure is not particularly limited. It is preferably from approximately 0.1 to 10 MPa, more preferably from approximately 0.1 to 5 MPa, and further preferably from approximately 0.3 to 5 MPa.

Those skilled in the art can freely determine the stirring efficiency, the reaction temperature, the amount of the catalyst employed, and the like for the catalytic hydrogenation reaction. The reaction may be conducted preferably at a temperature of from approximately −20 to 100° C., and more preferably from approximately 0 to 70° C.

In a particularly preferred embodiment, monatin(s), 4-hydroxy-4-(3-indolylmethyl)-glutamic acid(s) (including that or those in the salt form(s)) represented by the structural formula (3) can be produced by utilizing the process of the present invention.

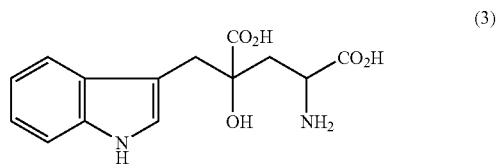

(3)

Specifically, in the process for producing a γ-hydroxyamino acid derivative in the present invention, a monatin (including that in the salt form) represented by the structural formula (3) can be produced by selecting a 3-indolylmethyl group as $R^1$, a hydrogen atom as $R^2$ and a hydrogen atom as $R^3$ respectively in the formulas.

The dihydroisoxazole derivatives represented by the formulae (1) and (4) may also take the form of salt.

As noted above, the monatin(s) (including that or those in the salt form(s)) are obtained by or via the process of the present invention (process for producing a γ-hydroxyamino acid derivative) in the form of a stereoisomer (optical isomer) or in the form of a mixture of plural optical isomers. Even a mixture of plural optical isomers can be used directly as a sweetening ingredient or optically purified by any conventional optical resolution method or the like (see, e.g., *Kirk-Othmer, Encyclopedia of Chemical Technology, 4th Ed.*, Wiley, NY, vol. 2, pp. 519-522, 1992; and P. Newman, *Optical Resolution Procedures for Chemical Compounds*, Optical Resolution Information Center, Riverdale, N.Y., 1978, both of which are incorporated herein by reference). Monatin(s) obtained by such purification or analogs thereof (including that or those in the salt form(s)) are also included naturally in those produced by the process of the present invention.

In the process of the present invention, the starting materials may be in the form of free compounds or salts, and both of them can be employed in the reaction used in the present invention. Likewise, the desired products produced in the present invention may be obtained in the form of free compounds or salts. When the desired products are produced in the form of salts as a result of the reaction in the present invention, they can be obtained in the form of salts as such or can easily be obtained in the form of free compounds by further conducting a conventional desalting step (free form-forming step from salt). Meanwhile, when the desired products are produced in the form of free compounds, they can be obtained in the form of free compounds or in the form of salts by further conducting a conventional salt-forming step. These are all included in the present invention.

The bases used to form salts are not particularly limited. For example, inorganic bases such as sodium hydroxide, potassium hydroxide, calcium hydroxide and sodium carbonate; and organic bases such as ammonia and amines may be used.

In another embodiment, the present invention provides a method for preparing a sweetener composition by mixing a sweetening effective amount of a compound of formula (2) or (3) with a food grade carrier or excipient or another sweetener, in which the compound of formula (2) or (3) has been prepared by the present method.

In another embodiment, the present invention provides a method for preparing a sweetened food or beverage by mixing a sweetening effective amount of a compound of formula (2) or (3) with a food or beverage, in which the compound of formula (2) or (3) has been prepared by the present method.

In the present methods for preparing a sweetener or a sweetened food or beverage, the exact amount of the compound formula (2) or (3) to be added to the food grade carrier or excipient, another sweetener, food, or beverage will depend on the exact identity of the compound of formula (2) or (3), including the degree of diastereomeric and optical purity, as well as the degree of sweetening desired. However, the determination of the amount of compound to add is well within the skill of the art.

Other features of the invention will become apparent in the course of the following descriptions of exemplary embodiments which are given for illustration of the invention and are not intended to be limiting thereof.

EXAMPLES

The $^1$H-NMR spectra were measured with a Bruker AVANCE 400 (400 MHz) spectrometer, and the MS spectra were measured with a Thermo Quest TSQ 700 spectrometer.

Example 1

Synthesis of diethyl 5-(RS)-(3-indolylmethyl)-4,5-dihydroisoxazole-3,5-dicarboxylate The above-referenced compound was obtained as a light yellow solid in a total yield of 66% by using the method described in C. W. Holzapfel et al., *Synthetic Communications*, vol. 24(22), pp. 3197-3211 (1994) with slight modification.

(NMR spectrum) $^1$H-NMR (CDCl$_3$, 400 MHz) δppm: 1.24 (3H, t), 1.30 (3H, t), 3.20 (1H, d), 3.46 (2H, dd), 3.61 (1H, d), 4.14-4.28 (2H, m), 7.11-7.21 (3H, m), 7.38 (1H, d), 8.23 (1H, br, s).

Example 2

Synthesis of 5-(RS)-(3-indolylmethyl)-4,5-dihydroisoxazole-3,5-dicarboxylic acid 1.03 g (3.0 mmols) of diethyl 5-(RS)-(3-indolylmethyl)-4,5-dihydroisoxazole-3,5-dicarboxylate was dissolved in a mixed solvent of 16 ml of ethanol and 4 ml of water. 290 mg (6.9 mmols) of lithium hydroxide monohydrate was added thereto, and the mixture was stirred at room temperature for 1 hour. The reaction solution was concentrated to a volume of ⅓ or so under reduced pressure, and 15 ml of water and 1N hydrochloric acid were added to adjust the reaction solution to a pH of from 1 to 2. The resulting solution was extracted three times with 20 ml of ethyl acetate, and the organic layer was washed with a saturated aqueous solution of sodium chloride and dried over anhydrous magnesium sulfate. The anhydrous magnesium sulfate was removed by filtration, and the filtrate was concentrated under reduced pressure to obtain 5-(RS)-(3-indolylmethyl)-4,5-dihydroisoxazole-3,5-dicarboxylic acid as a light yellow powder.

(NMR spectrum) $^1$H-NMR (DMSO-d$_6$, 400 MHz) δppm: 3.23 (1H, d), 3.34 (2H, s), 3.43 (1H, d), 6.98 (1H, t), 7.06 (1H, t), 7.19 (1H, d), 7.33 (1H, d), 7.57 (1H, d), 10.98 (1H, s).

Example 3

Synthesis of Monatin 380 mg (1.31 mmols) of 5-(RS)-(3-indolylmethyl)-4,5-dihydroisoxazole-3,5-dicarboxylic acid was dissolved in 8 ml of 28% aqueous ammonia solution, 200 mg of a 5% rhodium-active carbon catalyst was added thereto, and catalytic hydrogenation was conducted under a hydrogen pressure of 1 MPa for 16 hours. The catalyst was removed by filtration, and the filtrate was freeze-dried to obtain 336 mg of monatin and a small amount of DL-alanine as a by-product.

(MS spectrum) ESI-MS: 291 (M−H)$^-$. (NMR spectrum) $^1$H-NMR (400 MHz, D$_2$O) δppm:

(2S,4S) and (2R,4R) monatin ammonium salts
1.96 (1H, dd, J=11.8 Hz, J=15.2 Hz), 2.57 (1H, dd, J=1.9 Hz, J=15.2 Hz), 3.00 (1H, d, J=14.6 Hz), 3.20 (1H, d, J=14.6 Hz), 3.54 (1H, d, J=10.2 Hz), 7.04 (1H, t, J=7.2 Hz), 7.10 (1H, t, J=7.2 Hz), 7.10 (1H, s), 7.38 (1H, d, J=8.0 Hz), 7.62 (1H, d, J=8.0 Hz).

(2S,4R) and (2R,4S) monatin ammonium salts
2.11 (1H, dd, J=10.4 Hz, J=15.0 Hz), 2.37 (1H, d, J=15.4 Hz), 3.13 (2H, s), 3.88 (1H, d, J=9.8 Hz), 7.05 (1H, d, J=7.6 Hz), 7.14 (2H, s), 7.38 (1H, d, J=7.9 Hz), 7.63 (1H, d, J=7.9 Hz).

Example 4

Synthesis of Monatin 404 mg (1.40 mmols) of 5-(RS)-(3-indolylmethyl)-4,5-dihydroisoxazole-3,5-dicarboxylic acid was dissolved in 8 ml of 14% aqueous ammonia solution, 250 mg of a 5% rhodium-active carbon catalyst was added thereto, and catalytic hydrogenation was conducted under a hydrogen pressure of 1 MPa for 7 hours. The catalyst was removed by filtration, and the filtrate was freeze-dried to obtain 378 mg of monatin and a small amount of DL-alanine as a by-product.

Effect of the Invention

As has been thus far described, the method of the present invention can easily convert dihydroisoxazole derivatives to γ-hydroxyamino acid derivatives in high yield and further can easily produce monatins, one type of γ-hydroxyamino acid derivatives. Accordingly, the present invention can provide γ-hydroxyamino acid derivatives important as various synthetic intermediates, and monatins, materials with sweet taste having excellent properties especially as sweeteners or the ingredients thereof.

Thus, the present invention is quite useful industrially and particularly in the field of foods and pharmaceuticals.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for producing a γ-hydroxyamino acid derivative represented by the following formula (2) or a salt thereof:

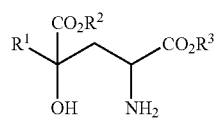

said process comprising subjecting a dihydroisoxazole derivative represented by the following formula (1) or a salt thereof to catalytic hydrogenation

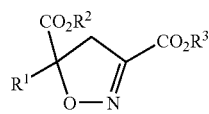

wherein $R^1$ is a 3-indolylmethyl group, which may be substituted with at least one of a halogen atom, a hydroxyl group, an alkyl group having up to 3 carbon atoms, an alkoxy group having up to 3 carbon atoms, and an amino group;

$R^2$ and $R^3$ each, independently of the other, represents a hydrogen atom, an alkyl group having up to 5 carbon atoms, or an aralkyl group having up to 12 carbon atoms; and each asymmetric carbon atom in formulae (1) and (2) may have a steric configuration of (R), (S) or (RS).

2. The process of claim 1, wherein in the formulae (1) and (2), $R^1$ is a 3-indolylmethyl group.

3. The process of claim 1, wherein said catalytic hydrogenation is conducted in the presence of at least one catalyst selected from the group consisting of rhodium catalysts, palladium catalysts, ruthenium catalysts, nickel catalysts, and platinum catalysts.

4. The process of claim 1, wherein said catalytic hydrogenation is conducted in the presence of a base.

5. The process of claim 1, wherein said catalytic hydrogenation is conducted in the absence of a base.

6. The process of claim 1, wherein said catalytic hydrogenation is conducted in a solvent selected from the group consisting of water, alcohols, and water-alcohol mixed solvents.

7. The process of claim 1, wherein said catalytic hydrogenation is conducted at a hydrogen pressure of from 0.1 to 5 MPa.

8. The process of claim 1, wherein in formula (1), $R^1$ is a 3-indolylmethyl group, $R^2$ is a hydrogen atom, and $R^3$ is a hydrogen atom, and a monatin represented by the following structural formula (3) or a salt thereof is produced

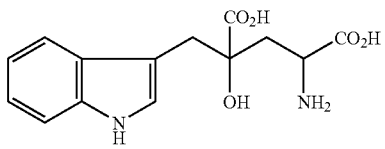

provided that said dihydroisoxazole derivative represented by the formula (1) may take the form of salt.

9. The process of claim 8, wherein said catalytic hydrogenation is conducted in the presence of at least one catalyst selected from the group consisting of rhodium catalysts, palladium catalysts, ruthenium catalysts, nickel catalysts, and platinum catalysts.

10. The process of claim 8, wherein said catalytic hydrogenation is conducted in the presence of a base.

11. The process of claim 8, wherein said catalytic hydrogenation is conducted in the absence of a base.

12. The process of claim 8, wherein said catalytic hydrogenation is conducted in a solvent selected from the group consisting of water, alcohols, and water-alcohol mixed solvents.

13. The process of claim 8, wherein said catalytic hydrogenation is conducted at a hydrogen pressure of from 0.1 to 5 MPa.

14. The process of claim 1, wherein said y-hydroxyamino acid derivative represented by formula (2) or salt thereof is enriched in the (2S,4S)- and/or the (2R,4R)-isomer.

15. A process for preparing a sweetener composition, comprising:

(1) catalytically reducing a dihydroisoxazole derivative represented by the following formula (1) or a salt thereof:

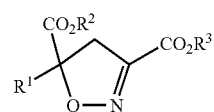

wherein $R^1$ is a 3-indolylmethyl group, which may be substituted with at least one of a halogen atom, a hydroxyl group, an alkyl group having up to 3 carbon atoms, an alkoxy group having up to 3 carbon atoms, and an amino group; and $R^2$ and $R^3$ each, independently of the other, represents a hydrogen atom, an alkyl group having up to 5 carbon atoms, or an aralkyl group having up to 12 carbon atoms, to obtain a γ-hydroxyamino acid derivative represented by the following formula (2) or a salt thereof:

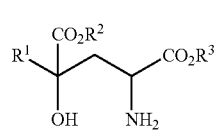

wherein $R^1$, $R^2$, and $R^3$ are as defined as above, and wherein each asymmetric carbon atom in formulae (1) and (2) may have a steric configuration of (R), (S) or (RS); and (2) mixing said γ-hydroxyamino acid derivative represented by formula (2) or a salt thereof with a food grade carrier or excipient or another sweetener.

16. The process of claim 15, wherein in the formulae (1) and (2), $R^1$ is a 3-indolylmethyl group.

17. The process of claim 15, wherein said γ-hydroxyamino acid derivative represented by formula (2) or salt thereof is enriched in the (2S,4S)- and/or the (2R,4R)-isomer.

18. A process for preparing a sweetened food or beverage, comprising:

(1) catalytically reducing a dihydroisoxazole derivative represented by the following formula (1) or a salt thereof:

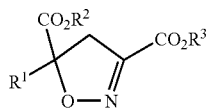

(1)

wherein $R^1$ represents a hydrogen atom, a carboxyalkyl group having up to 20 carbon atoms, an alkyl group having up to 20 carbon atoms, an aryl group having up to 20 carbon atoms, an aralkyl group having up to 20 carbon atoms, or an heterocyclic ring(s)-containing hydrocarbon group having up to 20 carbon atoms; and $R^2$ and $R^3$ each, independently of the other, represents a hydrogen atom, an alkyl group having up to 5 carbon atoms, or an aralkyl group having up to 12 carbon atoms, to obtain a γ-hydroxyamino acid derivative represented by the following formula (2) or a salt thereof:

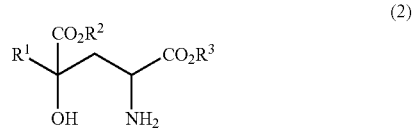

(2)

wherein $R^1$, $R^2$, and $R^3$ are as defined as above, and wherein each asymmetric carbon atom in formulae (1) and (2) may have a steric configuration of (R), (S) or (RS); and (2) mixing said γ-hydroxyamino acid derivative represented by formula (2) or a salt thereof with a food or beverage.

19. The process of claim 18, wherein in the formulae (1) and (2), $R^1$ is a 3-indolylmethyl group.

20. The process of claim 18, wherein said γ-hydroxyamino acid derivative represented by formula (2) or salt thereof is enriched in the (2S,4S)- and/or the (2R,4R)-isomer.

* * * * *

UNITED STATES PATENT AND TRADEMARK OFFICE
CERTIFICATE OF CORRECTION

PATENT NO. : 7,329,427 B2  Page 1 of 1
APPLICATION NO. : 10/397407
DATED : February 12, 2008
INVENTOR(S) : Yusuke Amino et al.

It is certified that error appears in the above-identified patent and that said Letters Patent is hereby corrected as shown below:

Column 5, line 45, insert --wherein-- before $R^1$.

Signed and Sealed this

Twelfth Day of August, 2008

JON W. DUDAS
*Director of the United States Patent and Trademark Office*